United States Patent [19]
Vesely

[11] Patent Number: 5,830,144
[45] Date of Patent: Nov. 3, 1998

[54] TRACKING DATA SHEATH

[76] Inventor: Ivan Vesely, 1216 Oakridge Dr., Cleveland Heights, Ohio 44121

[21] Appl. No.: 812,249

[22] Filed: Mar. 6, 1997

Related U.S. Application Data

[63] Continuation-in-part of Ser. No. 411,959, Mar. 28, 1995, Pat. No. 5,515,853.

[51] Int. Cl.⁶ ..................................................... A61B 8/14
[52] U.S. Cl. ........................................... 600/459; 600/466
[58] Field of Search ................................... 600/459, 374, 600/466, 470

[56] References Cited

U.S. PATENT DOCUMENTS

| | | |
|---|---|---|
| 4,173,228 | 11/1979 | VanSteenwyk et al. . |
| 4,304,239 | 12/1981 | Perlin . |
| 4,431,005 | 2/1984 | McCormick . |
| 4,444,195 | 4/1984 | Gold . |
| 4,499,493 | 2/1985 | Nishimura . |
| 4,522,212 | 6/1985 | Gelinas et al. . |
| 4,573,473 | 3/1986 | Hess . |
| 4,613,866 | 9/1986 | Blood . |
| 4,628,937 | 12/1986 | Hess et al. . |
| 4,649,924 | 3/1987 | Taccardi . |
| 4,697,595 | 10/1987 | Breyer et al. . |
| 4,699,147 | 10/1987 | Chilson et al. . |
| 4,777,955 | 10/1988 | Brayton et al. . |
| 4,812,976 | 3/1989 | Lundy . |
| 4,821,731 | 4/1989 | Martinelli et al. . |
| 4,899,750 | 2/1990 | Ekwall . |
| 4,922,912 | 5/1990 | Watanabe . |
| 4,932,414 | 6/1990 | Coleman et al. ................. 128/600.09 |
| 4,940,064 | 7/1990 | Desai . |

(List continued on next page.)

FOREIGN PATENT DOCUMENTS

| | | |
|---|---|---|
| 0 152 905 | 8/1985 | European Pat. Off. . |
| 92301264 | 2/1992 | European Pat. Off. . |
| 0 591 899 | 10/1993 | European Pat. Off. . |
| 3904914 | 8/1990 | Germany . |
| 41 19 150 | 12/1992 | Germany . |
| US94/08352 | 7/1994 | WIPO . |
| US94/11298 | 10/1994 | WIPO . |
| US95/01103 | 1/1995 | WIPO . |
| PCT/CA96/00194 | 3/1996 | WIPO . |

OTHER PUBLICATIONS

Meyer et al., Application of Sonomicrometry and Multidimensional Scaling to Cardiac Catheter Tracking, *Transactions on Biomedical Engineering*, vol. 44 No. 11, pp. 1061–1067, Nov. 1997.

Davis J.W., Improved Arrival Time Detection for Cardiac Pulse Transit Sonomicrometry, *Computers in Cardiology 1996*, pp. 145–459, 1996.

Morse, Wayne, Medical Electronics, *IEEE Spectrum*, pp. 99–102, Jan. 1997.

Josephson et al., Comparison of Endocardial Catheter Mapping with Intraoperative Mapping of Ventricular Tachycardia, *Circulation*, vol. 61, No. 2, pp. 395–404, 1980.

Josephson et al., Ventricular Tachycardia during Endothelial Pacing. II. Role of Pace–Mapping to Localize Origin of Ventricular Tachycardia, *The American Journal of Cardiology*, vol. 50, pp. 11–22, Jul. 1982.

Witkowski et al., An Automated Simultaneous Transmural Cardiac Mapping System, *American Journal of Physiology*, vol. 247, pp. H661–H668, 1984.

(List continued on next page.)

*Primary Examiner*—Marvin M. Lateef
*Assistant Examiner*—Maulin Patel
*Attorney, Agent, or Firm*—Benesch, Friedlander, Coplan & Aronoff LLP

[57] ABSTRACT

A tracking data sheath (20,20',100) arrangable on a variety of different surgical instruments (e.g., catheters and probes) to provide the surgical instruments with 3-D tracking capability. The tracking data sheath (20,20',100) being generally elastomeric or rigid for convenient installation and removal, and having transducers (30) and conductors (32) embedded therein.

20 Claims, 3 Drawing Sheets

U.S. PATENT DOCUMENTS

| | | |
|---|---|---|
| 4,945,305 | 7/1990 | Blood . |
| 5,000,190 | 3/1991 | Petre . |
| 5,012,814 | 5/1991 | Mills et al. . |
| 5,016,173 | 5/1991 | Kenet et al. ............................ 382/128 |
| 5,025,786 | 6/1991 | Siegel . |
| 5,041,973 | 8/1991 | Lebron et al. . |
| 5,042,486 | 8/1991 | Pfeiler et al. ............................ 128/653 |
| 5,054,492 | 10/1991 | Scribner et al. . |
| 5,054,496 | 10/1991 | Wen et al. . |
| 5,056,517 | 10/1991 | Fenici . |
| 5,081,993 | 1/1992 | Kitney et al. . |
| 5,104,393 | 4/1992 | Isner et al. . |
| 5,154,501 | 10/1992 | Svenson et al. . |
| 5,156,151 | 10/1992 | Imran . |
| 5,158,092 | 10/1992 | Glace . |
| 5,161,536 | 11/1992 | Vilkomerson et al. . |
| 5,172,699 | 12/1992 | Svenson et al. . |
| 5,220,924 | 6/1993 | Frazin . |
| 5,222,501 | 6/1993 | Ideker et al. . |
| 5,246,016 | 9/1993 | Lieber et al. . |
| 5,295,484 | 3/1994 | Marcus et al. . |
| 5,297,549 | 3/1994 | Beatty et al. . |
| 5,341,807 | 8/1994 | Nardella . |
| 5,357,956 | 10/1994 | Nardella . |
| 5,391,199 | 2/1995 | Ben-Haim . |
| 5,443,489 | 8/1995 | Ben-Haim . |
| 5,480,422 | 1/1996 | Ben-Haim . |
| 5,515,853 | 5/1996 | Smith et al. . |
| 5,517,990 | 5/1996 | Kalfas et al. . |
| 5,546,951 | 8/1996 | Ben-Haim . |

OTHER PUBLICATIONS

Fann et al., Endocardial Activation Mapping and Endocardial Pace–Mapping Using a Balloon Apparatus, *American Journal of Cardiology,* vol. 55, pp. 1076–1083, Apr. 1, 1985.

Tweddell et al., Potential Mapping in Septal Tachycardia: Evaluation of a New Intraoperative Mapping Technique; *Circulation,* vol. 80 (Supplement I), No. 3, pp. I–97–I–108, Sep. 1989.

Hauer et al., Endocardial Catheter Mapping: Wire Skeleton Techniques for Representation of Computed Arrhythmogenic Sites Compared with Intraoperative Mapping, *Circulation,* vol. 74. No. 6. pp. 1346–1354, Dec. 1986.

Pogwizd et al., Reentrant and Nonreentrant Mechanisms Contribute to Arrhythmogenesis During Early Myocardial Ischemia: Results Using Three–Dimensional Mapping, *Circulation Research,* vol. 61, No. 3, pp. 352–371, Sep. 1987.

Huang et al., Radiofrequency Catheter Ablation of the Left and Right Ventricles: Anatomic and Electrophysiologic Observations, *Pace,* vol. II, pp. 449–459, Apr. 1988.

Jackman et al., New Catheter Techniques for Recording Left Free–Wall Accessory Atrioventricular Pathway Activation, *Circulation,* vol. 78, No. 3, pp. 589–611, Sep. 1988.

Shenasa et al., Cardia Mapping, Part I: Wolff–Parkinson–White Syndrome, *Pace,* vol. 13, pp. 223–230, Feb. 1990.

Scheiman et al., Current Role of Catheter Ablative Procedures in Patients with Cardiac Arrhythmias, *Circulation,* vol. 83, No. 6, pp. 2146–2153, Jun. 1991.

Buckles et al., Computer–Enhanced Mapping of Activation Sequences in the Surgical Treatment of Supraventricular Arrhythmias, *Pace,* vol. 13, Pt. 1, pp. 1401–1407, Nov. 1990.

Tanigawa et al., Prolonged and Fractionated Right Arterial Electrograms During Sinus Rhythm in Patients with Paroxysmal Atrial Fibrillation and Sick Sinus Node Syndrome, *Journal of American College of Cardiologists,* vol. 17, No. 2, pp. 403–408, Feb. 1991.

Kaltenbrunner et al., Epicardial and Endocardial Mapping of Ventricular Tachycardia in Patients with Myocardial Infarction, *Circulation,* vol. 83, No. 3, pp. 1058–1071, Sep. 1991.

Masse et al., A Three–Dimensional Display for Cardiac Activation Mapping, *Pace,* vol. 14, Pt. 1, pp. 538–545, Apr. 1991.

Desai et al., Orthogonal Electrode Catheter Array for Mapping of Endocardial Focal Site of Ventricular Activation, *Pace,* vol. 14, Pt. 1, pp. 557–574, Apr. 1991.

Pollak et al., Intraoperative Identification of a Radiofrequency Lesion Allowing Validation of Catheter Mapping of Ventricular Tachycardia with a Computerized Balloon Mapping System, *Pace,* vol. 15, pp. 854–858, Jun. 1992.

Chen et al., Reappraisal of Electrical Cure of Atrioventricular Nodal Reentrant Tachycardia—Lesions from a Modified Catheter Albation Technique, *International Journal of Cardiology,* vol. 37, pp. 51–60, 1992.

Chen et al., Radiofrequency Catheter Albaltion For Treadment of Wolff–Parkinson–White Syndrome–Short–and Long–Term Follow–up, *International Journal of Cardiology,* vol. 37, pp. 199–207, 1992.

Scheinman, North American Society of Pacing and Electrophysiology (NASPE)Survey on Radiofrequency Catheter Ablation: Implications for Clinicians, Third Party Insurers, and Government Regulatory Agencies, *Pace,* vol. 15, pp. 2228–2231, Dec. 1992.

Silka et al., Phase Image Analysis of Anomalour Ventricular Activation in Petiatric Patients with Pre–excitation Syndromes or Ventricular Tachycardia, *American Heart Journal,* vol. 125, No. 2, Pt. 1, pp. 372–380, Feb. 1993.

Josephson, Clinical Cardiac Electrophysiology: Techniques and Interpretations, 2md Ed., pp. 566–580, 608–615, 770–783, *Lea & Febiger,* Malvern, Pa., 1993.

Holt et al., Ventricular Arrhythmias—A Guide to Their Localization, *British Heart Journal,* vol. 53, pp. 417–430, 1985.

Joseph et al., Role of Catheter Mapping in the Preoperative Evaluation of Ventricular Tachycardia, *American Journal of Cardiology,* vol. 40, pp. 207–220, Jan. 1982.

Kucher et al., Electrocardiographic Localization of the Site of Ventricular Tachycardia in Patients with Prior Myocardial Infarction, *JACC,* vol. 13, No. 4 pp. 893–900.

Page, Surgical Treatment of Ventricular Tachycardia: Regional Cryoablation Guided by Computerized Epicardial and Endocardial Mapping, *Circulation,* vol. 80, (Supplement I), No. 3, pp. I124–I–134, Sep. 1989.

5,830,144

TRACKING DATA SHEATH

RELATED APPLICATIONS

The present application is a continuation-in-part (CIP) of co-pending PCT Application No. WO96/31753, which is a continuation-in-part (CIP) of U.S. application Ser. No. 08/411,959, filed Mar. 28, 1995, now U.S. Pat. No. 5,515,853. Both applications are incorporated herein by reference.

FIELD OF THE INVENTION

The present invention relates generally to a tracking device attachable to a surgical instrument, and more particularly to a tracking device in the form of a sheath attachable to a surgical instrument for tracking the position of same.

BACKGROUND OF THE INVENTION

In medical procedures, such as catheterizations, intraluminal intraoperative ultrasound, endoscopic procedures and laparoscopic procedures, catheters, probes, needles, sensors and other instruments are introduced into a patient's body. In most cases, such as in the use of mapping and ablating catheters, these instruments are visualized inside the body using continuous fluoroscopy by creating a shadow of the instrument as the physician manipulates the instrument moving it within the body. In the case of intra operative ultrasound, transesophageal ultrasound, intraluminal and laparoscopic ultrasound, an imaging head is inserted into the patient's body. The position of the imaging head is not known, and orienting and localizing is done only based on the image that is being generated by the imaging head. Some orienting, however, is possible from the length of the tube inserted into the patient, and the radial orientation of the device. The local orientation and location of the imaging head, however, are not typically available with existing systems.

An ultrasound based catheter guidance system as described in U.S. Pat. No. 5,515,853 and incorporated herein by reference, can display the position and motion of catheters as a 3-D graphic. This system makes use of transit time ultrasound to measure the distance between an array of ultrasonic transducers. Using the time-of-flight principle of high frequency sound waves, it is possible to accurately measure distances within an aqueous medium, such as inside the body of a living being during a surgical procedure. High frequency sound, or ultrasound, is defined as vibrational energy that ranges in frequency from 100 kHz to 10 MHz. The device used to obtain three-dimensional measurements using sound waves is known as a sonomicrometer. Typically, a sonomicrometer consists of a pair of piezoelectric transducers, (i.e., one transducer acts as a transmitter while the other transducer acts as a receiver). The transducers are implanted into a medium, and connected to electronic circuitry. To measure the distance between the transducers, the transmitter is electrically energized to produce ultrasound. The resulting sound wave then propagates through the medium until it is detected by the receiver.

The transmitter typically takes the form of a piezoelectric crystal that is energized by a high voltage spike, or impulse function lasting under a microsecond. This causes the piezoelectric crystal to oscillate at its own characteristic resonant frequency. The envelope of the transmitter signal decays rapidly with time, usually producing a train of six or more cycles that propagate away from the transmitter through the aqueous medium. The sound energy also attenuates with every interface that it encounters.

The receiver also typically takes the form of a piezoelectric crystal (with similar characteristics to the transmitter piezoelectric crystal), that detects the sound energy produced by the transmitter and begins to vibrate in response thereto. This vibration produces an electronic signal in the order of millivolts, that can be amplified by appropriate receiver circuitry.

The propagation velocity of ultrasound in an aqueous medium is well documented. The distance traveled by a pulse of ultrasound can therefore be measured simply by recording the time delay between the instant the sound is transmitted and when it is received.

As indicated above, some of the transducers are mounted to the catheters (or other instrument) inserted into the body, and other transducers (i.e. reference transducers) are affixed to the patient at a fixed location, and provide external and/or internal reference frames. A large matrix of distances between many combinations of transducers is obtained many times per second, and then converted into x,y,z coordinates for each transducer. The motion of the catheter fitted with such ultrasonic transducers can then be tracked in 3-D space, relative to the position of the external and/or internal reference transducers.

Catheters themselves are typically polymeric tubes with some diagnostic or therapeutic component incorporated into the distal segment of the catheter. To convert a conventional catheter into one that can be tracked has involved the remanufacture of the catheter such that it incorporates several ultrasonic transducers along its length to determine the position of the catheter relative to the reference transducers located elsewhere on or inside the patient. For low cost, disposable instruments, such as catheters, such integration is often appropriate, particularly, since the wires for interconnecting the transducers take up significant space and need to be integrated into the body of the catheter in an efficient way.

Other instruments inserted into the body, such as those incorporating ultrasound imaging elements, may be expensive and need to be sterilized and reused many times. There is also a very large number of variations in instrument configuration, particularly in those instruments that are used for laparoscopic surgery. Accordingly, it may not be feasible to incorporate localization and tracking transducers into all of these instruments during their manufacture. Moreover, ultrasonic transducers have a finite life span, and thus require periodic replacement. In view of the foregoing, it would be desirable if a whole range of instruments could be retrofitted with the ultrasonic transducers in a manner that does not require remanufacture, modification or permanent alteration thereof.

The present invention overcomes these and other drawbacks of prior art devices and provides a tracking data sheath for quickly and easily modifying an instrument to include tracking capabilities.

SUMMARY OF THE INVENTION

According to the present invention there is provided a tracking data sheath which is attachable to a surgical or diagnostic instrument to allow the position of the instrument to be tracked. The sheath is generally elastomeric or rigid, and may be conveniently fitted to an instrument.

It is an object of the present invention to provide a tracking data sheath, which is easily attachable to a variety of different types of diagnostic and surgical instruments, including catheters, probes, sensors, needles, and the like.

It is another object of the present invention to provide a tracking data sheath which is easily removable from the instrument for convenient replacement and disposal.

It is still another object of the present invention to provide a tracking data sheath which may be pre-sterilized.

It is still another object of the present invention to provide a tracking data sheath which is easily fitted to a variety of instruments having various dimensions.

It is yet another object of the present invention to provide a tracking data sheath which is durable and can withstand considerable force.

These and other objects will become apparent from the following description of the preferred embodiment taken together with the accompanying drawings and the appended claims.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein.

DETAILED DESCRIPTION OF THE PREFERRED EMBODIMENT

Figure 1:
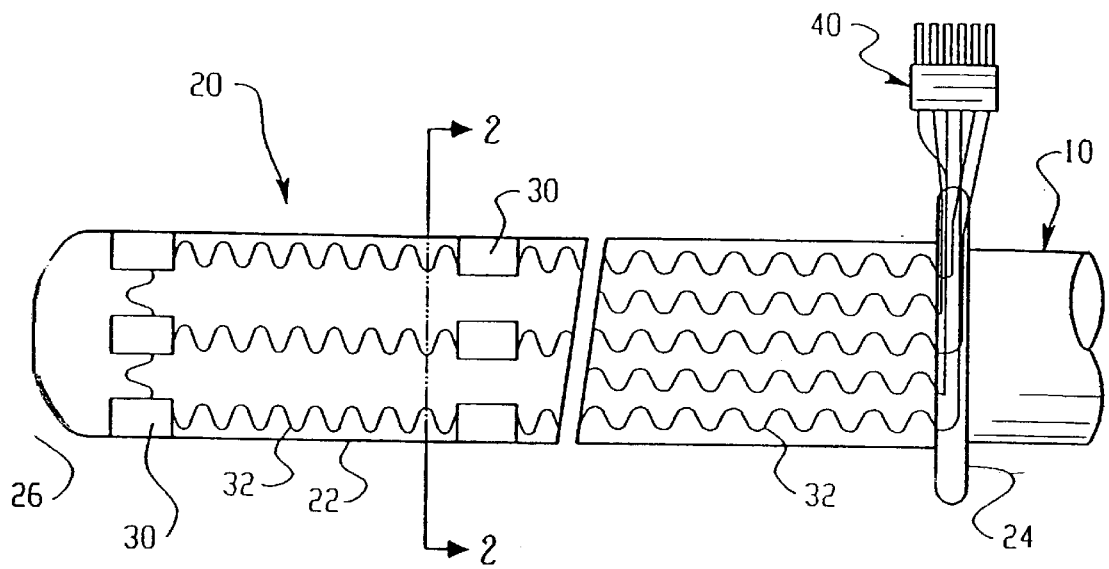
FIG. 1 is a side perspective view of the tracking data sheath according to a preferred embodiment of the present invention.

Referring now to the drawings wherein the showings are for the purposes of illustrating a preferred embodiment of the invention only and not for purposes of limiting same, FIG. 1 shows a tracking data sheath 20 arranged on an instrument 10. It should be noted that instrument 10 may take the form of various type of instruments including catheters, ultrasound probes and endoscopes.

Tracking data sheath 20 includes an elongated body portion 22 having a proximal end 24 and a distal end 26. In the embodiment shown in FIG. 1, distal end 26 is closed. However, in many cases, distal end 26 will be open to enable diagnostic or therapeutic components located at the distal end of instrument 10 to remain active and unobstructed.

Figure 2:
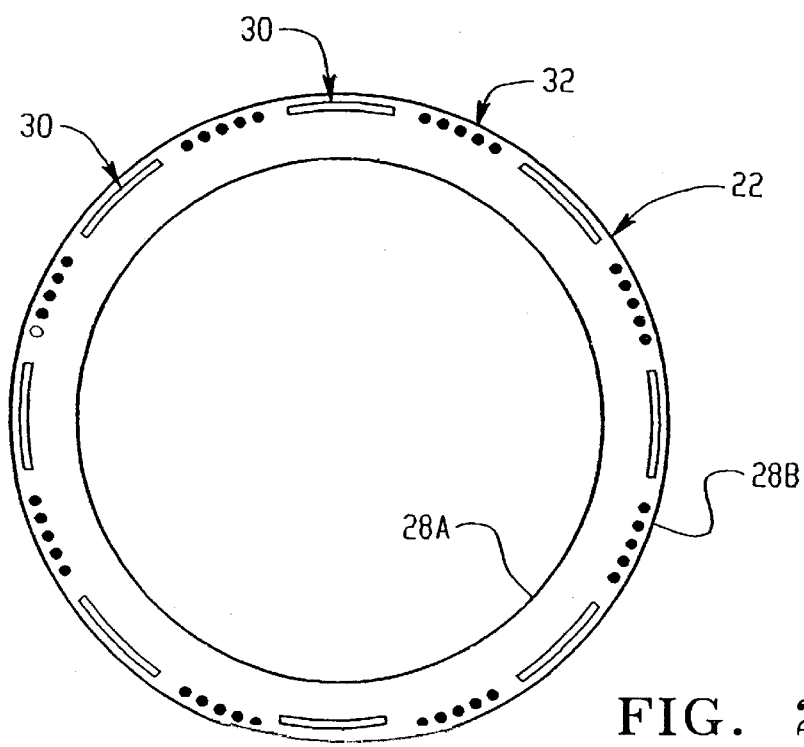
FIG. 2 is a sectional view taking along lines 2—2 of FIG. 1.

Body portion 22 has an inner wall 28A and an outer wall 28B, as shown in FIG. 2. Transducers 30 and conductors 32 are preferably cast, imbedded, or laminated between walls 28A and 28B. Accordingly, there is no remaining void between wall 28A and 28B. Transducers 30 are preferably piezoelectric transducer crystals consisting of PZT or PVDF material. Conductors 32 preferably take the form of very thin and flexible wires that are cast, imbedded, or laminated into body portion 22 in a wavy or tortuous coiled fashion, so as to stretch with sheath 20 appropriately during rolling, unrolling and other manipulations, as will be explained below.

Conductors 32 connect transducers 30 to each other and with a connector 40 at the proximal end 24. Conductors 32 are used to carry electrical signals for "firing" a transmitter transducer, and to carry electrical signals generated by a receiver transducer when it receives a sound wave from a transmitter transducer. It should be understood that the term "firing" refers to the action of energizing a transducer to oscillate by sending a voltage spike or impulse function to the transducer. Transducers 30 are preferably interconnected together in a plurality of "rings" within walls 28A and 28B to enable several individual transducers 30 to be "fired" in unison as a ring. The electrical signals and sound waves described above are collectively referred to as tracking signals.

Connector 40 connects sheath 20 to a 3-D tracking and imaging system. Accordingly, conductors 32 communicates electrical signals to and from transducers 30 and the 3-D tracking and imaging system.

In a first embodiment of the present invention, body portion 22 is preferably constructed from an appropriate elastomeric material, to form a rubberized polymeric tubular housing, resembling a sleeve or sock. Body portion 22 is preferably as thin as possible to facilitate rolling off and unrolling onto instrument 10, as will be explained below. Accordingly, sheath 20 will be elastic to enable body portion 22 to easily fit over of instrument 10, and also to prevent any constraint on the flexibility of instrument 10, if it is intended to flex.

It should be appreciated that sheath 20 may have various lengths and diameters to facilitate use on a wide range of instrument configurations, while maintaining sufficient tightness to prevent movement of transducers 30 relative to instrument 10. In addition, a temporary adhesive such as tape may be used to ensure that the segment of sheath 20 containing transducers 30 does not slide up or down on instrument 10, thus compromising the 3-D registration of the position of instrument 10 relative to a tracking environment.

Figure 3:
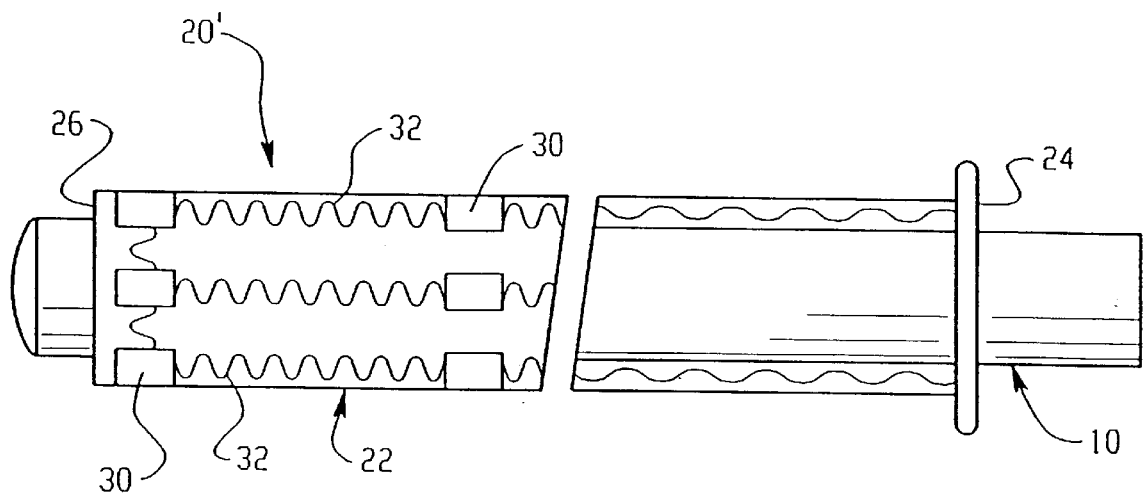
FIGS. 3 and 4 are side perspective views of a tracking data sheath according to an alternative embodiment of the present invention.
Figure 4:
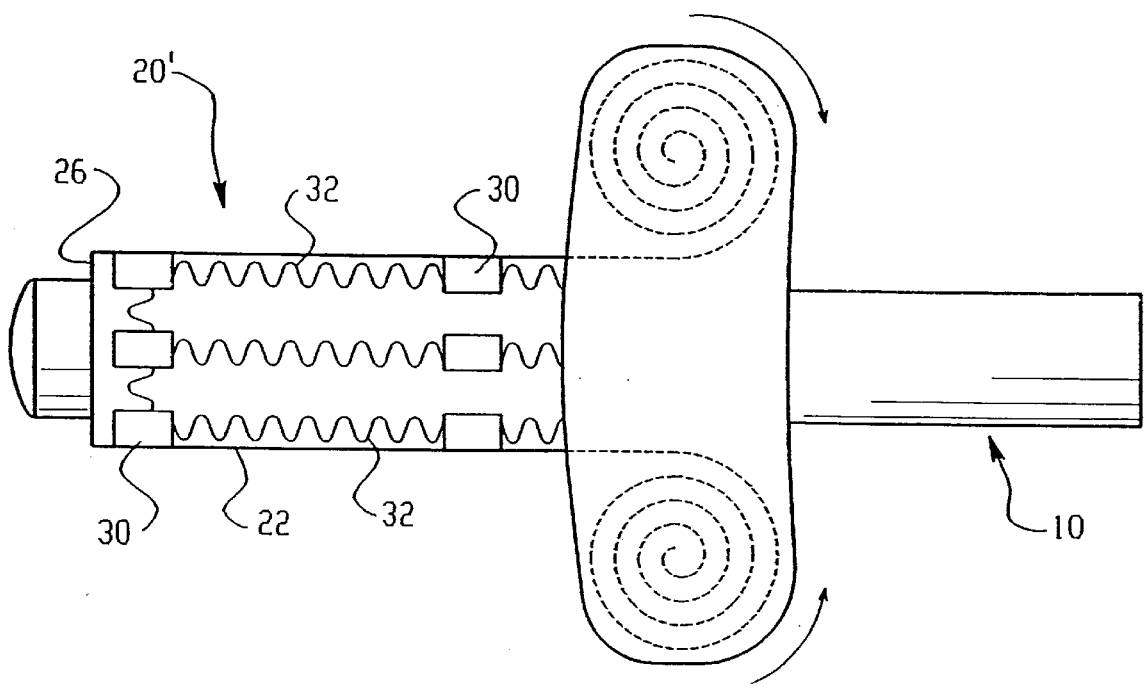

Turning now to FIGS. 3 and 4, there is shown an alternative embodiment of the present invention. In this respect, a tracking data sheath 20' is shown having an open distal end 26. The other elements of tracking data sheath 20' are the same as tracking data sheath 20, shown in FIGS. 1 and 2. Because distal end 26 is open, any diagnostic or therapeutic components located at the distal end of instrument 10 can remain active and unobstructed.

FIG. 4 illustrates the fitting of tracking data sheath 20' to instrument 10. It should be noted that the following fitting procedure also applies to sheath 20 described above. Sheath 20 is mounted to instrument 10 and unrolled over instrument 10. It should be noted that it may be desirable to supply sheath 20' pre-sterilized. Accordingly, sheath 20' may be rolled up along its longitudinal axis for convenient storage and to facilitate the insertion of instrument 10 into sheath 20', and the unrolling of sheath 20' over the length of instrument 10.

Figure 5:
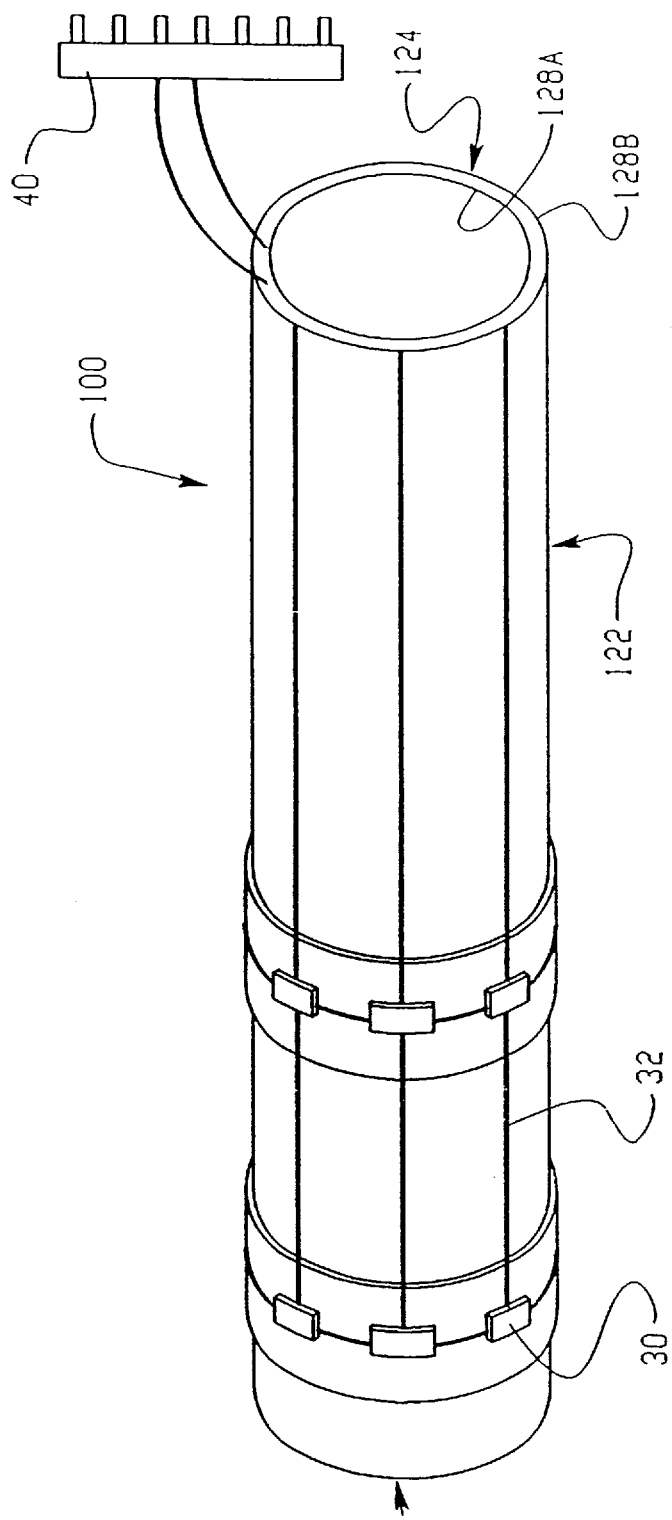
FIG. 5 is a side perspective view of a tracking data sheath according to a second alternative embodiment of the present invention.

Referring now to FIG. 5, there is shown another embodiment of the present invention. In this embodiment, tracking data sheath 100 has an elongated body portion 122 having a proximal end 124 and a distal end 126. In the embodiment shown in FIG. 5, both ends 124 and 126 are open. Importantly, body portion 122 is a generally rigid member, preferably formed of a plastic material. Body portion 122 has an inner surface 128A and an outer surface 128B. Transducers 30 and conductors 32 are preferably cast, embedded or laminated into body portion 122. It should be appreciated that since body portion 122 is a generally rigid member, conductors 32 need not be arranged in a wavy or coiled fashion. A connector 40 located at the proximal end 124 connects to a 3-D tracking and imaging system.

It should be appreciated that transducers 30 may take the form of a ring-shaped array of crystals (FIG. 5), or a segmented or unsegmented cylindrical single crystal. This configuration enables ultrasound energy to radiate at a large angle away from perpendicular to the axis of the cylinder, such that the crystal array functions as a line source of ultrasound energy, or as a collection of point sources, each radiating ultrasound energy in a fan substantially away from the plane of the cylinder.

Tracking data sheath 100 may be inserted into a bodily structure (e.g., an organ) under 3-D tracking. Subsequently, an instrument (e.g., ablation probe) is inserted inside of sheath 100. In this manner, sheath 100 facilitates positioning of the instrument to the desired location, without the need to permanently attach a tracking system to the instrument. After the instrument is located at the desired position, sheath can be slid upwards along the shaft of the instrument, and out of the way of the treatment area.

The foregoing is a description of the specific embodiment of the present invention. It should be appreciated that this embodiment is described for purposes of illustration only and that numerous alterations and modifications may be practiced by those skilled in the art without departing from the spirit and scope of the invention. For instance, while a preferred embodiment of the present invention has been described with reference to a system using ultrasonic sound waves to determine position, electromagnetic waves are suitable substitutes. Accordingly, the ultrasonic transducers can be suitably replaced by electromagnetic transducers. It is intended that all such modifications and alterations be included insofar as they come within the scope of the invention as claimed or the equivalents thereof.

I claim:

1. A tracking data sheath attachable to an instrument means comprising:
    an elongated body member having an outer portion and an inner portion;
    transducer means for generating tracking signals, the transducer means including a plurality of piezoelectric elements interconnected to form one or more transducers rings, wherein the transducer rings are arranged between the outer and inner portions;
    conductor means for interconnecting the plurality of piezoelectric elements and communicating tracking signals to and from the plurality of piezoelectric elements; and
    connector means for connecting the tracking data sheath to an associated position tracking system, the connector means connected to said conductor means.

2. A tracking data sheath according to claim 1, wherein said connector means is located external to said elongated body member.

3. A tracking data sheath according to claim 1, wherein said piezoelectric elements include PZT.

4. A tracking data sheath according to claim 1, wherein said body member is formed of an elastomeric material.

5. A tracking data sheath according to claim 1, wherein said body member is formed of a rigid material.

6. A tracking data sheath according to claim 1, wherein said plurality of piezoelectric elements are cast, imbedded, or laminated between said outer and inner portions.

7. A tracking data sheath according to claim 1, wherein said conductor means are wavy wires.

8. A tracking data sheath according to claim 1, wherein said sheath further comprises:
    adhesive means for adhering said body member to said instrument means.

9. A method for configuring a surgical instrument with a position tracking sheath including a generally elastomeric body member having at least one open end, and position indicating means for indicating the position of the position tracking sheath, the method comprising:
    rolling the sheath along the longitudinal axis thereof into a rolled-up position;
    inserting the surgical instrument into the open end of the sheath over the surgical instrument;
    unrolling the sheath from the rolled-up position onto the surgical instrument; and
    connecting the position indicating means with a position tracking system.

10. A method for configuring a surgical instrument with a position tracking sheath according to claim 9, wherein said position indicating means includes transducer means located in said elastomeric body member, the transducer means including a plurality of piezoelectric elements interconnected to form one or more transducer rings, wherein each piezoelectric element is fired individually by said position tracking system.

11. A method for configuring a surgical instrument with a position tracking sheath according to claim 9, wherein said position indicating means includes transducer means located in said elastomeric body member, the transducer means including a plurality of piezoelectric elements interconnected to form one or more transducer rings, wherein each piezoelectric element of the same transducer ring is fired in unison by said position tracking system.

12. A method for configuring a surgical instrument with a position tracking sheath including a generally rigid body member having at least one open end, and position indicating means for indicating the position of the position tracking sheath, the method comprising:
    inserting the surgical instrument into the sheath; and
    connecting the position indicating means with a position tracking system, wherein the position indicating means includes transducer means integrally formed in the sheath, the transducer means including a plurality of piezoelectric elements interconnected to form one or more transducer rings.

13. A method for configuring a surgical instrument with a position tracking sheath according to claim 12, wherein each piezoelectric element is fired individually by said position tracking system.

14. A method for configuring a surgical instrument with a position tracking sheath according to claim 12, wherein each piezoelectric element of the same transducer ring is fired in unison by said position tracking system.

15. A tracking data sheath attachable to an instrument means comprising:
    an elongated body member;
    transducer means for generating tracking signals, the transducer means including a plurality of electromagnetic elements interconnected to form one or more transducer rings;
    conductor means for interconnecting the plurality of electromagnetic elements and communicating tracking signals to and from the plurality of electromagnetic elements; and
    connector means for connecting the tracking data sheath to an associated position tracking system.

16. A tracking data sheath according to claim 15, wherein said body member is generally elastomeric.

17. A tracking data sheath according to claim 15, wherein said body member is generally rigid.

18. A position tracking device attachable to an instrument means comprising:

an elongated body member;

transducer means for generating position tracking signals, the transducer means including a plurality of interconnected transducer elements;

conductor means for interconnecting the plurality of transducer elements and communicating tracking signals to and from the plurality of transducer elements; and connector means for connecting the tracking data sheath to an associated position tracking system.

19. A position tracking device according to claim 18, wherein said transducer elements are piezoelectric elements.

20. A position tracking device according to claim 18, wherein said transducer elements are electromagnetic elements.

* * * * *